United States Patent [19]
Prevost et al.

[11] 3,985,624
[45] Oct. 12, 1976

[54] DEVICE FOR CONTINUOUS SAMPLING, ESPECIALLY IN A DISTILLATION COLUMN FOR TOPPING CRUDE PETROLEUM

[75] Inventors: Michel Prevost, Heyrieux; Bernard Vourron, Oullins, both of France

[73] Assignee: Institut Francais du Petrole, des Carburants et Lubrifiants et Entreprise de Recherches et d'Activities Petrolieres Elf, Paris, France

[22] Filed: May 27, 1975

[21] Appl. No.: 581,347

[30] Foreign Application Priority Data
May 30, 1974 France .............................. 74.18871

[52] U.S. Cl. ............................... 196/132; 23/253 A; 23/254 R; 73/421.5 R; 73/422 R; 203/1
[51] Int. Cl.² ...................... B01D 3/42; C10G 7/10; G01N 33/22
[58] Field of Search .......... 23/232 R, 253 R, 253 A, 23/254 R; 73/421.5 R, 422 R; 196/132; 203/1, DIG. 1, 3

[56] References Cited
UNITED STATES PATENTS

| | | | |
|---|---|---|---|
| 2,703,015 | 3/1955 | Sykes | 73/422 R |
| 3,177,125 | 4/1965 | Berger | 196/132 X |
| 3,517,557 | 6/1970 | Grauger et al. | 73/421.5 |
| 3,641,821 | 2/1972 | Neuberger et al. | 23/254 R X |
| 3,765,226 | 10/1973 | Strickland et al. | 73/422 R X |

*Primary Examiner*—Morris O. Wolk
*Assistant Examiner*—Michael S. Marcus
*Attorney, Agent, or Firm*—Sughrue, Rothwell, Mion, Zinn and Macpeak

[57] ABSTRACT

A sampling circuit connected directly to the distillation column consists of a primary loop formed by a sampling tube which penetrates into the column in a region of expansion and vaporization and is equipped with means for limiting the velocity of the vapor collected therein and for separating the entrained liquid fraction if necessary. The sampling circuit further comprises a condenser and a filter, the condensate being returned to the column by a circulating pump and a withdrawal of condensate being effected by a secondary loop for supplying an analyzing device in parallel.

1 Claim, 4 Drawing Figures

DEVICE FOR CONTINUOUS SAMPLING, ESPECIALLY IN A DISTILLATION COLUMN FOR TOPPING CRUDE PETROLEUM

This invention relates to a device for continuously sampling a given fraction or "cut" of a crude petroleum within an atmospheric distillation or topping column, especially in the zone in which said petroleum which is fed into the column at suitable pressure and temperature undergoes abrupt expansion with vaporization of the greater part of the flow, the remaining liquid fraction or residuum being recovered from the bottom of the column.

The aim of the invention is to provide a simple device for taking a sample which is exactly representative of the vaporized fraction of the crude petroleum being processed while excluding the liquid residuum, this vaporized fraction being more particularly intended to be supplied to an analytical and measuring instrument. The results provided by said instrument serve to plot the crude petroleum distillation curve or so-called TBP curve (true boiling point) within the minimum periods of time. The TBP curve gives the yield of each by-product of the distillation process, that is to say the relative quantity which can be withdrawn from the column, as defined by an initial temperature and a final temperature. In this apparatus, the vaporized fraction of the crude petroleum being processed is withdrawn by the device in accordance with the invention in a region in which said fraction is precisely representative of the general composition of the crude petroleum with the exception of the liquid residuum. Said vaporized fraction is separated into its components and the hold-up time within the apparatus in the case of each component is related to its distillation temperature by a given relation, the overall result thereby achieved being to determine successively the characteristic points of the curve to be plotted, said curve being employed for the purpose of controlling the distillation column in accordance with the specifications of the by-products to be obtained. The device makes it possible at the same time to determine the quantitative value of the fraction which is withdrawn and then analyzed with respect to the total composition of the sample. This permits graduation of the scale of yields on the distillation curve and extrapolation of said curve in the zone of the liquid residuum, the final curve being thus representative of the entire sample which is being processed.

To this end, the device under consideration essentially comprises a sampling circuit which is directly connected to the column and comprises on the one hand a primary loop formed by a sampling tube of substantial length which penetrates transversely into the column in that region of said column in which expansion and vaporization of the greater part of the crude petroleum take place, said tube being open at that extremity which penetrates into the column and being provided with means for limiting the velocity of the vapor collected in the tube and separating the liquid fraction which may have been entrained, a condenser located outside the column and connected to the sampling tube for condensing the sampled vapor, a filter mounted at the outlet of the condenser and a circulating pump for returning the condensate to the column and an additional secondary loop for effecting a withdrawal from the condensate in order to supply an analyzing device in parallel.

The means for limiting the velocity of the vapor collected in the sampling tube are preferably constituted by and end-piece mounted at the open extremity of the tube within the column and comprising a casing having side-walls provided with a series of coaxial annular collars in interengaged relation and forming baffle-plates, said casing being coupled with a curved pipe which forms a drain-trap siphon.

By making use of a sampling tube which penetrates directly into the column, the device in accordance with the invention thus offers the advantage of ensuring continuous sampling of the cut to be analyzed under conditions which are readily conducive to the establishment of a quantitative balance within the sampling zone in order to determine the percentage of the fraction sampled with respect to the total flow rate of injected crude petroleum. Said balance entails in particular a measurement of the flow of liquid reflux within the column itself and a comparison with all the flows which take place within the column.

Further advantages and characteristic features of a sampling device in accordance with the invention will become apparent from the following description of one example of construction which is given by way of indication without any implied limitation, reference being made to the accompanying drawings, wherein.

Figure 1:
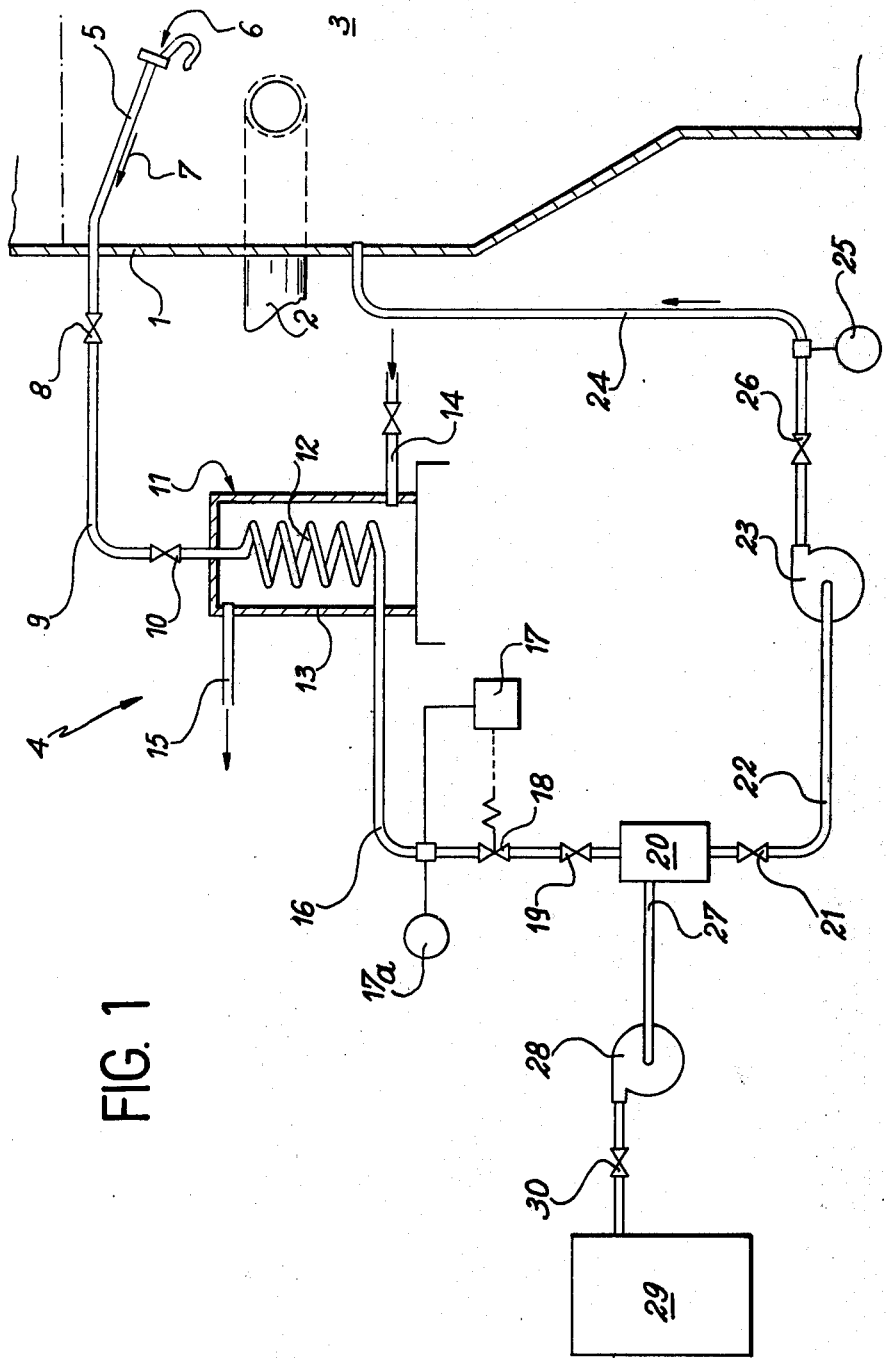
FIG. 1 is a diagrammatic view of the device in accordance with the invention.

In FIG. 1, the reference numeral 1 designates a lateral portion of the vertical-axis shell of a distillation column of conventional type for topping crude petroleum. The petroleum to be distilled within the column is supplied through a feed pipe 2 which opens into a zone 3 or so-called expansion zone in which the greater part of the petroleum is vaporized. The vapor passes upward within the column and undergoes fractional distillation with condensation of the by-products on horizontal plates (not shown in the drawings). The non-vaporized fraction of the crude petroleum which is fed into the zone 3 or residuum is collected in liquid form at the bottom of the column.

In order to carry out sampling of the fraction thus vaporized within the zone 3, a continuous sampling circuit 4 is employed in accordance with the invention. Said circuit mainly comprises a primary loop constituted by a sampling tube 5 which penetrates transversely into the interior of the column, said tube being provided with an end-piece 6, the constructional detail of which will be explained hereinafter. The vapor collected in the sampling tube 5 flows out of this latter in the direction of the arrow 7 and is collected in a pipe 9 after passing through an isolating valve 8. Said valve is connected by means of a valve 10 to a condenser 11 comprising mainly a tube coil 12 in which the vapor coming from the pipe 9 is condensed by circulating a coolant within an external casing 13, said coolant being fed to the condenser through a pipe 14 and removed through a pipe 15. At the outlet of the condenser 11, the condensate has a flow rate of the order of 120 to 150 l/hr under the practical conditions of operation and is passed through a pipe 16 fitted with a safety device 17 which operates an electrovalve 18 when the temperature of the condensate becomes higher than a predetermined threshold, for example as a result of a fault condition of the condenser, said device being connected to a measuring unit 17a which is mounted on the pipe. Provision is also made within said pipe for a shut-off valve 19 for stopping the flow in the direction of a filter 20. At the outlet of said filter, the condensate is recirculated in a pipe 22 after passing through a further isolating valve 21. Said pipe 22 is connected to a circulating pump 23 which discharges into a pipe 24 and this latter is connected to the column 1 in a region located beneath the pipe 2 in the expansion zone 3. In consequence, the withdrawn fraction must be continuously returned into the column and practically in its entirety. A regulating valve 26 serves to control the delivery of the circulating pump 23, this delivery being measured by means of an apparatus 25.

Part of the condensate which is thus circulated within the primary loop of the circuit 4 is then withdrawn, preferably at the level of the filter 20, by means of a pipe 27 and a pump 28 which supplies an analyzer 29. A valve 30 regulates the rate of inflow to the analyzer.

Figure 2:
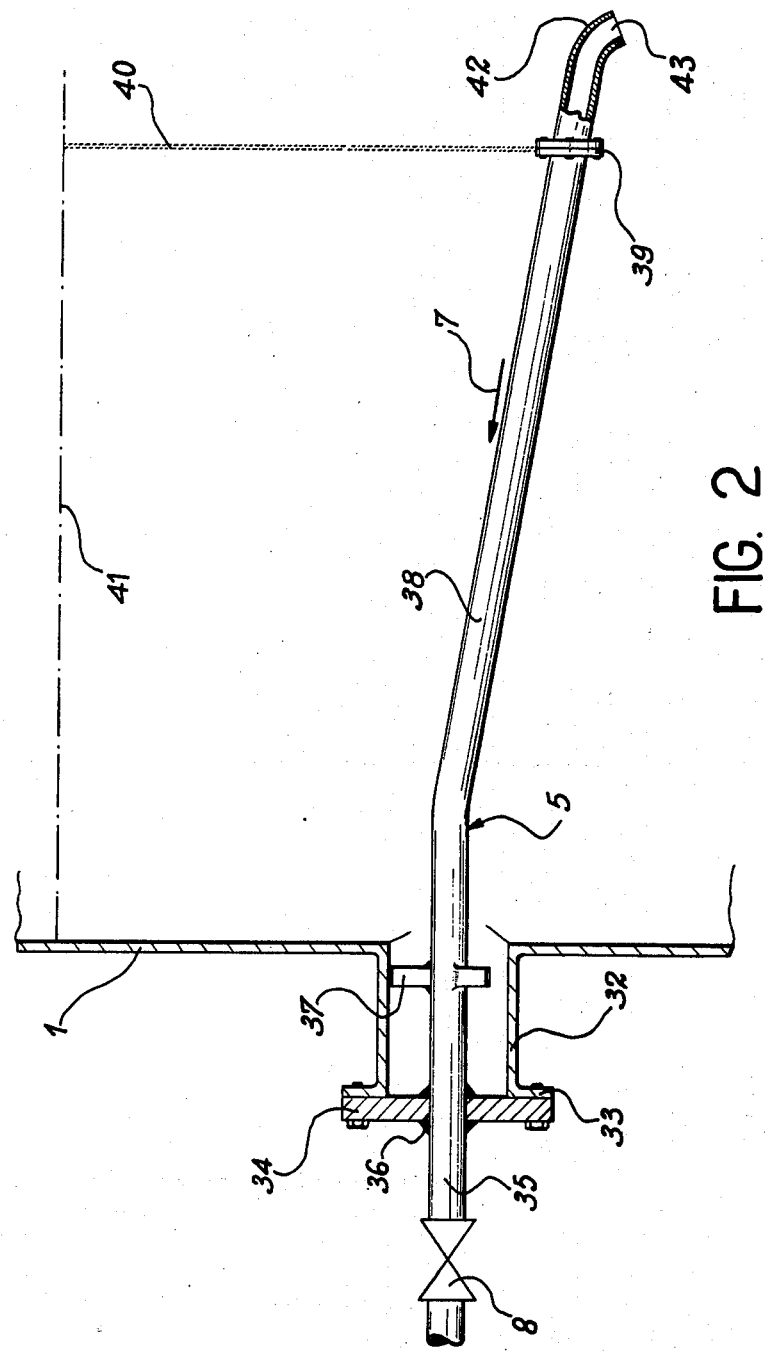
FIG. 2 is a detail view to a larger scale illustrating the sampling tube.

Referring now to FIG. 2, the method which can be adopted for the practical construction of the sampling tube 5 is shown in greater detail. Said sampling tube penetrates into the interior of the shell of the column 1 through an access sleeve 32 which is integral with said shell and terminates in an annular shoulder 33 on which is fixed a positioning flange 34, said flange being in turn secured to the rear portion 35 of the sampling tube 5 by means of weld fillets 36. Centering of the sampling tube 5 within the sleeve 32 is ensured by means of transverse lugs 37 which are applied against the internal wall of the sleeve. Said rear portion 35 of the sampling tube has an extension in the form of an inclined portion 38 within the interior of the column 1. Said extension 38 is directed downwards within the column and terminates in a coupling flange 39 for supporting the sampling tube in overhung position by means of a tierod 40 suspended from a structure 41, the constructional detail of which has little direct bearing on the invention. The coupling flange 39 also serves to connect the sampling tube to an elbowed end-piece 42 having an open extremity 43 which is directed downwards within the column and through which the sampled vapor penetrates into the tube 5 and then escapes towards the exterior in the direction of the arrow 7.

Figure 3:
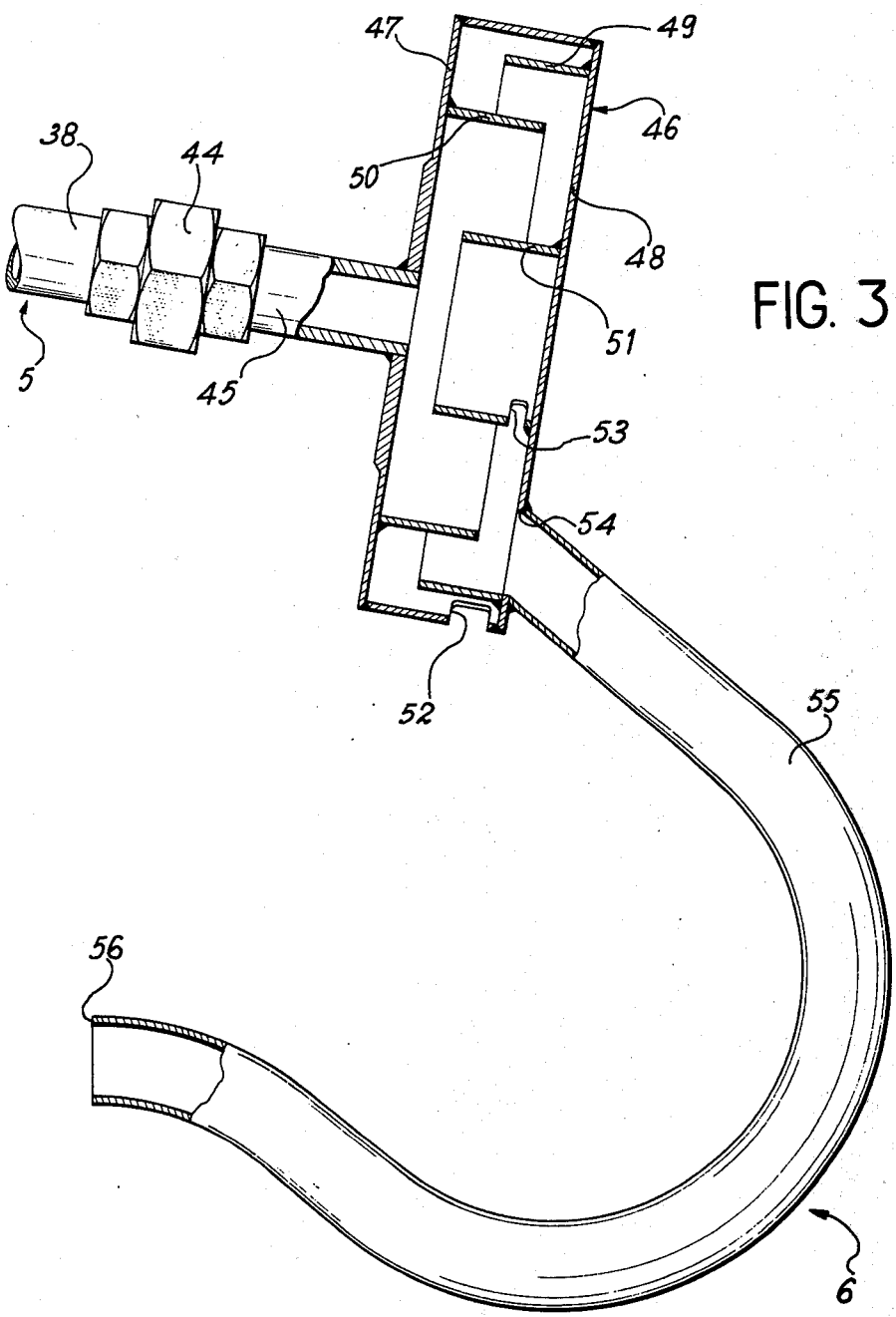
FIG. 3 is a transverse sectional view to an even larger scale showing one form of construction of an end-piece mounted at the extremity of the sampling tube.

There is shown in greater detail in FIG. 3 an alternative form of construction of the end-piece which can be mounted at the extremity of the inclined portion 38 of this latter. In this alternative embodiment, said portion 38 terminates in a connecting element 44 for a tube 45 which is extended by a casing 46. Said casing is delimited by two parallel side-walls 47 and 48, the side-wall 47 being traversed by the tube 45. Coaxial annular collars 49, 50 and 51 are mounted between the two side-walls and form a series of baffle-plates within the interior of the casing 46 so as to limit the velocity of the vapor as this latter penetrates into the casing through lateral apertures 52 and 53 which open towards the bottom of the column. Said baffle-plates have a further effect in that any droplets of the liquid residue which has not been vaporized within the zone 3 are prevented from being entrained within the sampling tube. As an advantageous feature, the casing 46 is provided in its side-wall 48 with an opening 54 to which is connected an elbowed pipe 55 forming a drain siphon, the open lower extremity 56 of which serves to drain continuously from the casing the liquid fraction which may have been entrained by the vapor. In an alternative design, it would be possible to fill the casing 46 with a metallic packing or the like which facilitates draining of the liquid.

Figure 4:
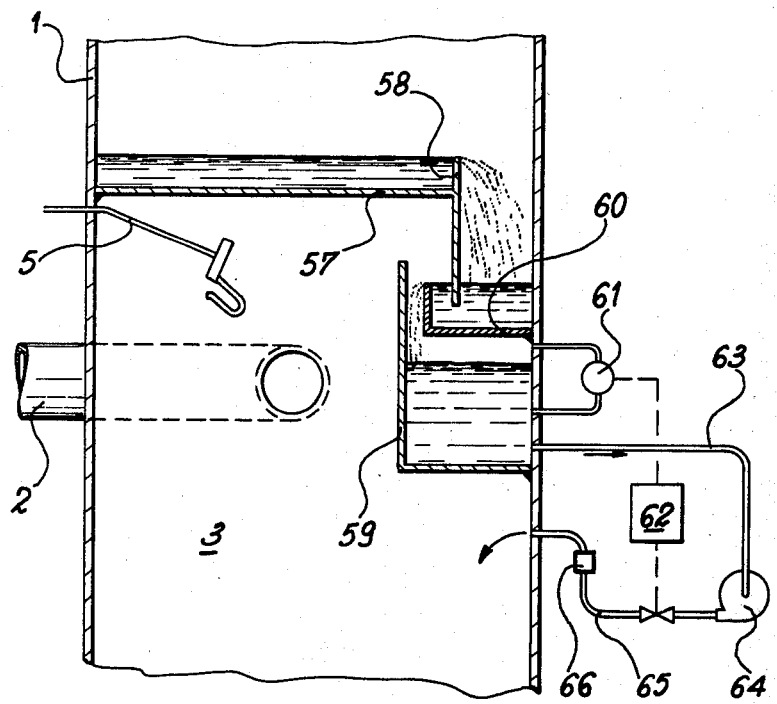
FIG. 4 is a diagrammatic view of an auxiliary apparatus for determining the value of the liquid reflux rate within the distillation column.

Finally, FIG. 4 illustrates an auxiliary apparatus which is associated with the sampling device described in the foregoing and serves to determine the liquid reflux rate within the column and by means of a total balance to determine the exact quantity of vapor sampled by the sampling tube with respect to the quantity of crude petroleum which is fed into the column for processing.

As can be seen from this figure, the expansion zone 3 is delimited in particular at the top portion thereof by the first horizontal distillation plate 57 which is in turn delimited on one side by a baffle-plate 58 over which flows the liquid fraction which has not been withdrawn and is condensed on said plate. Said liquid fraction is collected within the column 1 in a lateral container 59 which is secured against the internal wall of the column after flowing over a weir 60, the design function of which is to stabilize the level within the container 59. The position of this level is measured by means of a detector 61 or like instrument which produces action on a regulator 62. The liquid within the container 59 is then withdrawn through a pipe 63 connected to a circulating pump 64, the liquid being discharged by this latter into the pipe 65 and returned into the column. The delivery of said pump as measured by the flow meter 66 and controlled by the regulator 62 is so determined as to ensure that the level within the container 59 is maintained constant. By virtue of these arrangements, the flow rate of the stream which is fed back into the column therefore corresponds exactly to the flow rate of the stream which is poured continuously from the plate 57. From a knowledge of this flow rate, of the flow rate of the different streams withdrawn from the column and of the flow rate of the crude petroleum at the inlet, it is possible to deduce the quantitative balance and especially the value of the vaporized fraction by means of either of the two expressions:

$$\frac{D1 + \Sigma D_{sn}}{D_B} \quad (1)$$

$$\frac{DB - DR + D1}{D_B} \quad (2)$$

in which:
  $D_{sn}$ is the flow rate of the side stream of order $n$,
  $D1$ is the liquid reflux rate as measured in the manner indicated in the foregoing,
  $DB$ is the flow rate of crude petroleum being processed,
  $DR$ is the flow rate of the liquid residuum.

There is thus provided a device for continuous sampling, especially in a distillation column for topping crude petroleum, which offers the advantage of permitting direct feed to a chromatographer analyzer. The results provided by said analyzer in turn permit rapid determination of the distillation curve of the petroleum to be processed, the sampled fraction being representative of the petroleum with the exception of the liquid fraction or residuum which cannot be analyzed by the chromatographic apparatus. It is also possible at the same time to determine the quantitative value of this fraction with respect to the total composition of a sample. The curve plotted by means of these elements can therefore be graduated directly in yields in the case of the single sampled fraction, then extrapolated for the portion corresponding to the liquid residuum, the final curve being then representative of the entire sample.

It is readily apparent that the invention is not limited to the example of construction which has been more especially described with reference to the accompanying drawings but extends on the contrary to all alternative forms.

What we claim is:

1. A distillation column having a device for the continuous sampling of a vaporized fraction of crude petroleum, said device comprising sampling means directly connected to said column and including a sampling tube of substantial length which penetrates transversely into the column in that region of the column in which expansion and vaporization of the greater part of the crude petroleum takes place, said tube being open at that extremity which penetrates into the column and being provided with means for limiting the velocity of the vapor collected in the sampling tube and separating the liquid fraction which may have been entrained, a condenser located outside the column and connected to the sampling tube for condensing the sampled vapor and pipe means including a filter mounted at the outlet of the condenser and a circulating pump for returning the condensate to the column and withdrawing means connected to said filter means for withdrawing a portion of the condensate to supply an analyzing device, said means for limiting the velocity of the vapor collected in the sampling tube comprising an end piece mounted at the open extremity of the sampling tube within the column and including a casing having an annular wall and side walls, said annular wall being provided with vapor inlet and one of said side walls having outlet means connected to and communicating with said open extremity of said sampling tube, baffle means secured to said side walls within said casing and comprising a pair of coaxially opposed overlapping spaced apart annular collars and drain means comprised of a curved outlet pipe connected to the other of said side walls of said casing adjacent the bottom thereof to form a draintrap siphon.

* * * * *

UNITED STATES PATENT AND TRADEMARK OFFICE
CERTIFICATE OF CORRECTION

PATENT NO. : 3,985,624
DATED : October 12, 1976
INVENTOR(S) : Michel PREVOST et al It is certified that error appears in the above–identified patent and that said Letters Patent are hereby corrected as shown below:

IN THE HEADING:

Under "Assignee", delete

"Institut Francais du Petrole, des
Carburants et Lubrifiants et
Entreprise de Recherches et
d'Activities Petrolieres Elf", and insert --Entreprise de Recherches et
d'Activites Petrolieres ELF--.

Signed and Sealed this

Nineteenth Day of April 1977

[SEAL]

Attest:

RUTH C. MASON
*Attesting Officer*

C. MARSHALL DANN
*Commissioner of Patents and Trademarks*